United States Patent [19]
Blake et al.

[11] Patent Number: 5,498,547
[45] Date of Patent: Mar. 12, 1996

[54] METHOD AND DEVICE FOR THE DETERMINATION OF POLYMERIC BIGUANIDES IN AQUEOUS FLUIDS

[75] Inventors: Kenneth A. Blake; Chauncey O. Rupe, both of Elkhart, Ind.; Carol A. Terry, Cassopolis, Mich.

[73] Assignee: Environmental Test Systems, Inc., Elkhart, Ind.

[21] Appl. No.: 248,296

[22] Filed: May 24, 1994

Related U.S. Application Data

[63] Continuation-in-part of Ser. No. 53,782, Apr. 28, 1993, abandoned.

[51] Int. Cl.⁶ .................................................. G01N 33/00
[52] U.S. Cl. .......................... 436/111; 436/124; 436/169; 436/904
[58] Field of Search ............................ 422/55–58, 82.05, 422/82.09; 436/86, 111, 124, 169, 904

[56] References Cited

U.S. PATENT DOCUMENTS

| | | | |
|---|---|---|---|
| 2,986,453 | 5/1961 | Collins | 23/253 |
| 3,063,812 | 11/1962 | Collins | 23/230 |
| 3,095,277 | 6/1963 | Free | 23/253 |
| 3,438,737 | 4/1969 | Atkinson | 23/230 |
| 4,092,115 | 5/1978 | Rupe et al. | 23/230 R |

*Primary Examiner*—David A. Redding
*Attorney, Agent, or Firm*—Harry T. Stephenson

[57] ABSTRACT

A test method and device is described for determining biguanides in aqueous fluids such as swimming pool water which involve contacting the fluid with a matrix incorporating a pH sensitive indicator material which exhibits the biguanide error effect. A buffer is advantageously used to maintain the test system within a defined constant pH range to eliminate the effect of pH changes on the test system.

13 Claims, 1 Drawing Sheet

U.S. Patent    Mar. 12, 1996    5,498,547
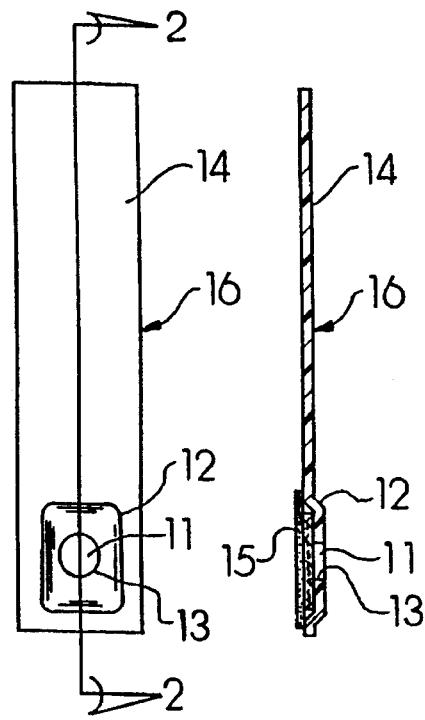
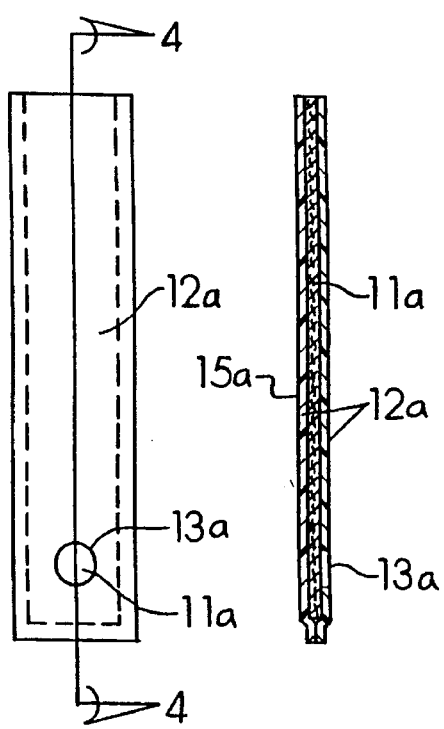
FIG. 1    FIG. 2    FIG. 3    FIG. 4
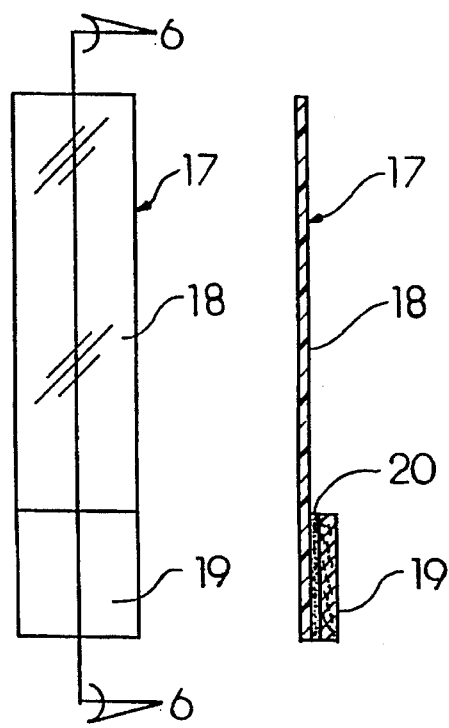
FIG. 5    FIG. 6

5,498,547

METHOD AND DEVICE FOR THE DETERMINATION OF POLYMERIC BIGUANIDES IN AQUEOUS FLUIDS

RELATIONSHIP TO COPENDING APPLICATIONS

This application is a continuation-in-part of U.S. application Ser. No. 053,782 filed 28 Apr. 1993 now abandoned.

FIELD OF THE INVENTION

The present invention relates to dry reagent test compositions incorporated into matrices which are useful in the determination of polymeric biguanides in aqueous fluids. More specifically it relates to unitized colorimetric dry reagent test devices which when contacted with aqueous test fluids which contain polymeric biguanides give a visual or instrumental indication of the presence and amount of such biguanide in the fluid being tested.

BACKGROUND OF THE INVENTION

Polymeric biguanides have been known for some time to have antibacterial and antifungal properties. More recently, such materials have been found to be useful in not only preventing the growth of bacteria and fungi but to be effective in controlling the growth of algae in swimming pool water. These materials are currently being presented to the pool operator as a safer and more effective alternative to the use of chlorine in sanitizing recreational pool water.

The use of disinfecting or sanitizing materials such as chlorine and biguanides requires that safe and effective concentration levels be maintained in the host fluids. The usual method for doing this involves routinely taking a sample of such fluid and subjecting it to an accepted testing procedure. Laboratory testing is the best possible alternative; however, home owners and swimming pool maintenance personnel usually do not have access to laboratories and must rely on a field test. The present field tests for biguanide concentration levels in swimming pool water involve a liquid test kit which requires that a representative sample of water be taken from the pool and drops of the liquid reagent be added thereto. Any change in the color of the water sample is then compared to a color chart or color comparator and the concentration level of the biguanide in the water is calculated. The present liquid drop tests are difficult to use and read and, for the most part, are not sufficiently accurate.

DESCRIPTION OF THE PRIOR ART

U.S. Pat. No. 4,014,676 describes polymeric biguanides, methods of preparation of such materials and the application thereof to prevent the growth of microorganisms, including algae, in swimming pool water. The concept of using protein error pH sensitive indicators to make dip and read reagent strip testing devices for the determination of proteins is disclosed in numerous patents dating back to the early 1960's. Examples of such patents include, U.S. Pat. Nos. 2,986,453; 3,063,812; 3,095,277; 3,121,612; 3,438,737; and U.K. Patent Specifications Nos. 814,223 and 826,066. Moreover, the concept of using a protein error indicator to make a test device for determining an analyte other than protein is likewise known. Although not specifically stated to utilize a protein error indicator, U.S. Pat. No. 3,973,090 discloses and claims the use of an indicator such as bromphenol blue and a buffer to make a test device for determining ethylene glycol in automobile and truck coolant fluids.

Patent disclosures and scientific literature relating to the construction of test devices utilizing a paper or polymeric matrix to contain a test reagent composition and a carrier to house the matrix and control or direct the test fluid to or through the matrix are almost too numerous to present here. The most relevant however are: U.S. Pat. Nos. 3,420,205 and 3,620,677 which concern sheath enclosed, reagent impregnated test devices for detecting analytes such as chlorides using a wicking, chromatography-type mechanism; and, U.S. Pat. Nos. 3,811,840 and 4,092,115 which disclose concentrating devices wherein fluid is directed through an opening or aperture in which a reagent composition is immobilized in order to concentrate the analyte in the device window where the color response is read.

SUMMARY OF THE INVENTION

The present invention basically involves utilizing the unexpected discovery that polymeric biguanides bind or immobilize, in situ, certain indicator materials in a matrix when contacted with a solution containing such a biguanide. This, coupled with the discovery that biguanides exert an effect similar to the protein error effect on certain pH sensitive indicator materials, allows such a device to be very effectively used as a field test device for the determination of polymeric biguanides.

The device and method involve incorporating a test reagent composition comprising a pH sensitive indicator material having a biguanide error effect in an absorbent matrix and contacting the matrix with the fluid to be tested. If biguanide is present in the test fluid, it binds with the indicator material in the matrix, substantially immobilizing such indicator therein and causing it to exhibit a color in or on the matrix in relation to the amount of biguanide present. Since the indicator is substantially entrapped at least in or on the surface of the matrix upon binding with the polymeric biguanide, larger amounts of test fluid can be passed through or across the matrix, allowing a substantial increase in sensitivity over a simple dip and read test strip device. In other words, the binding effect of the biguanide prevents the indicator from being leeched away from the area of the matrix in which the color reaction is read.

It has been found advantageous to include a buffer in the test reagent composition for maintaining the pH of the test fluid and the test composition at a predetermined level depending on the indicator material being utilized. This ensures that the color reaction produced in the matrix is due to the effect of the biguanide in the test fluid as opposed to simply a change in pH of the test fluid itself.

BRIEF DESCRIPTION OF THE DRAWINGS

FIGS. 1, 3 and 5 are front views of specific embodiments of test devices described in the present specification.

FIGS. 2, 4 and 6 are longitudinal sectional views taken along the lines 2, 4 and 6 respectively of the test devices shown in FIGS. 1, 3 and 5 respectively.

DESCRIPTION OF THE PREFERRED EMBODIMENTS

The biguanides referred to herein are linear polymers, the preferred material being polyhexamethylene biguanide, having an average molecular weight of about from 1100 to 1800. The antimicroorganism and particularly the algae inhibiting activity of these substances is described in U.S. Pat. No. 4,014,676. The method of preparation of such compounds is described in U.K Patent Specifications 702,268 and 1,152,243.

As indicated in the Summary of the Invention, the methodology and devices of the present invention basically involve incorporating an indicator material which responds to the presence of biguanides in a matrix and contacting this matrix with the fluid being tested. These indicator materials are pH sensitive colorimetric indicators or dyestuffs which normally change from one color to another over a defined range of pH values; however, when the pH environment is maintained constant at a defined pH value substantially within this normal range and polymeric biguanides are present, this normal range is shifted and a measurable color change is exhibited which is proportional to the presence and amount of biguanide in the fluid being tested. In other words, if an indicator normally changes from one color to another in a pH range of from 6 to 7, by keeping the pH of the fluid being tested constant to a value within this range, i.e. 6.7, by subjecting the same indicator to the presence of biguanide, it may change in a range of from 6.5 to 7.5 and thus exhibit a color change due to the presence of the polymeric biguanide. As used herein, the expression "change from one color to another" includes not only a change in color but also a change in intensity of a particular color.

This phenomenon of pH color change range shifting frequently occurs when pH indicators are used in the presence of proteins such as albumin and in such a situation it is known as the protein error of indicators effect. This concept forms the basis for many of the dip and read reagent strip and liquid tests for determining proteins in urine and other biological fluids.

In the present invention, it has been found that many of the pH sensitive indicator materials which exhibit protein error also respond to the presence of biguanides by shifting their normal ranges from one set of pH values to another. This will be called herein the "biguanide error of indicators effect". Although the exact mechanism for this effect is not known, it has been found that indicators such as bromothymol blue, bromophenol blue, bromocresol green, bromochlorophenol blue, bromocresol purple, 3,4,5,6-tetra-bromophenolsulfonephthalein, tetra-bromophenolphthalein ethyl ester, tetrabromophenol blue, and 3'3"5'5" -tetraiodophenolsulfonephthalein exhibit this effect and can be used in the reagent compositions of the present invention. The concentration of indicator used in the test composition is not critical; however, it has been found that concentrations of about from 0.0001M to 1.67M are effective in preparing such test compositions.

As previously noted it is advantageous to use a buffer to keep the pH of the test fluid contacting the test composition constant during the reaction of the biguanide with the indicator material. The exact pH at which the test system is buffered depends on the particular indicator material being utilized. Usually it has been found that a pH is selected for the buffer which is substantially within the range of pH values in which the indicator is normally responsive to a change in pH. To use the previous example wherein the indicator normally changes from one color to another over a range of from 6.0 to 7.0, it would be preferable to set the buffer at a pH within this range and depending on the sensitivity desired, the value would be set closer to one end or the other of such range. In this example, since the biguanide shifted the range upward, it would be preferable to set the pH closer to the upper end or edge limit of the range, which would in effect create a more sensitive test system.

Buffers such as TRIS/HCl, TRIS/phosphate, HEPES, EPPES, phthalic acid, malic acid, citric acid/sodium citrate, sodium phosphate, monobasic and dibasic, aspartic acid and oxalic acid may be used and it has been found that concentrations of about from 0.001M to 4M are effective.

An alternative but less facile method of utilizing a buffer with the present test method and device, is to add the buffer to the aqueous test fluid prior to contacting the device with the test fluid sample. Although involving more steps, such a method could be advantageously used if stability problems are encountered or additional buffering capacity is required which cannot be achieved by combining the buffer in the test reagent composition along with the indicator material.

As indicated above, the present invention involves the incorporation of the test reagent composition in an absorbent or bibulous matrix at least a portion of which has a substantially flat surface area which defines a test reaction area in which the color exhibited by the indicator material due to the presence of biguanide in the test fluid can be observed and measured. Matrix materials such as filter paper, synthetic fibers, gels, membranes, polymeric materials and so forth may be used to contain the test reagent composition. Absorbent paper is the preferable material and usual techniques are used to incorporate or impregnate the test reagent composition in the matrix. A common method is to dissolve or suspend the test reagent composition, usually comprising the colorimetric indicator material, in a solvent, dip the matrix into the reagent fluid whereby the matrix absorbs a portion of the fluid and thereafter drying the matrix at an elevated temperature or allowing it to dry at room temperature. Freeze drying may also be utilized to remove the solvent from the impregnated matrix. The resulting matrix then uniformly contains the dried residue of the test reagent composition. Other techniques such as incorporating the test reagent composition in a gel and forming the gel into thin layers on a support may also be utilized. For ease of use, the matrix containing the test reagent composition is in its simplest embodiment attached to a support handle such as sheet plastic which results in the so-called dip and read test devices in widespread use in the medical and environmental testing areas.

For relatively high concentrations, such as over about 50 ppm biguanide, the above described test device may simply be dipped into the solution or fluid being tested and upon removal, the color exhibited visually compared to a standardized color chart of known concentrations of biguanide. For less concentrated solutions, the test device may be dipped into the fluid and moved back and forth through the test fluid causing more fluid to come into contact with the test reagent thus increasing the sensitivity of the device. For lower concentrations yet of biguanide, such as about 10 ppm or less, the matrix may be contained in a holder therefor which contains a defined opening through which a measured amount of the test fluid is caused to pass thus increasing the contact volume and the sensitivity of the system.

In order to further increase the amount of fluid coming into contact with the test reagent composition, the matrix containing the composition may be attached to or backed up with additional absorbent material which in effect pulls more test fluid through or across the test reagent matrix.

For additional accuracy and to remove any subjectivity from the test system, the color exhibited in the test reaction area of the matrix may be read by a reflectance type colorimeter and the concentration of biguanide electronically determined by using an algorithm contained within the colorimeter.

Referring now to the drawings, FIGS. 1 and 2 represent an embodiment of the test device of the present invention for determining medium concentrations of biguanides in test fluids. The device comprises an elongated holder 16 of plastic which is formed with a rectangular offset well 12 at one end thereof and an integral handle portion 14 making up the remainder of this holder. A matrix 11 in the form of a square piece of absorbent paper impregnated with indicator material is positioned in the well and secured therein by means of a square of pressure sensitive adhesive tape 15 which completely covers and with well portion 12 forms a sheath for the matrix 11. An aperture 13 of limited area in holder 16 is positioned in the center of well 12 and contiguous to the flat surface of matrix 11 which allows the test fluid to enter the device to the extent of the absorptivity of the matrix 11. The test reagent composition is impregnated into or coated on the matrix 11 such that the aperture 13 covers a defined sample exposure area on the flat surface of the matrix through which the test fluid sample will flow.

FIGS. 3 and 4 represents another embodiment of the test devices of the present invention, this one being designed to have additional sensitivity for determining medium to low concentrations of biguanide in test fluids. Assuming that the devices shown in FIGS. 1 and 3 are about the same overall physical size, the matrix portion of the one shown in FIG. 3 being longer will absorb more test fluid and therefore function as a concentrator of test fluid in the opening thereof. This device comprises an elongated matrix 11a laminated between two elongated strips 12a and 15a sealed along both side edges and one end edge to form a sheath for said matrix. A test reagent composition comprising at least an indicator material exhibiting the biguanide error effect is incorporated into matrix 11a at least in the end portion thereof adjacent to the sealed end and an aperture or circular opening is positioned contiguous to the reagent impregnated end portion of the matrix, the aperture again defining the test fluid sample exposure area of the matrix. It is preferable that the plastic sheath material used in fabricating the devices shown in FIGS. 1 and 3 be made of an opaque plastic material so that only the color developed in the aperture can be observed and compared to a color chart or read by a reflectance colorimeter.

Finally, FIGS. 5 and 6 represent a standard reagent test strip 17 consisting of an elongated transparent semirigid plastic film handle 18 to which is attached a test reagent composition impregnated matrix pad 19 using a double faced adhesive tape layer 20.

The test devices shown in FIGS. 1 and 3 are used simply by immersing a device into a test fluid such that the fluid covers the aperture or opening in the sheath, allowing the fluid to completely saturate the matrix and observing the color formed in the aperture. As indicated above, this color can then be compared to a color chart to correlate the color to a biguanide concentration. The device shown in FIGS. 5 and 6 is simply dipped into the test fluid for a predetermined period of time, such as 10 to 30 seconds, removed and read against a standardized color chart. For additional sensitivity the strip may be dipped into the fluid and moved back and forth through the test fluid to enable more analyte to come in contact with the test reagent composition.

EXAMPLE 1

A 50% ethanolic solution of 0.028% 3,4,5,6-tetrabromophenolsulfonephthalein and 0.2M Tris/HCl, pH 8.5, was impregnated into Schleicher & Schuell grade 740E absorbent paper and dried at 95° C. The dried paper was cut into 0.5 in. squares and the squares inserted into devices as shown in FIGS. 1 and 2 of the drawings. The finished test devices were utilized by inserting the lower end of the device into the test fluid such that the aperture is covered by the test fluid. The devices were allowed to remain in the test fluid for thirty (30) seconds.

Contact with varying concentrations of polymeric biguanide (polyhexamethylene biguanide) produced the following results:

| Parts per million Biguanide | Color |
| --- | --- |
| 0 | Pale Cream |
| 15 | Pale Purple |
| 30 | Lavender |
| 50 | Deep Lavender |
| 70 | Purple |

EXAMPLE 2

Example 1 was repeated except that the impregnating solution comprised 0.1M 3', 3"-dibromothymolsulfonephthalein and 0.5M phosphate buffer at a pH of 8.0. Contact of test devices with biguanide as in Example 1 resulted in a color response of pale cream (0 ppm biguanide) to increasing intensities of green with good differentiation between the concentration levels of biguanide.

EXAMPLE 3

Example 1 was repeated except that a 0.2% solution of 3', 3", 5', 5"-tetrabromophenolsulfonephthalein (TBPSP) and 1.4M citrate buffer, pH 3.2 was used as an impregnating solution. When test devices were contacted with varying concentration solutions of biguanide as in Example 1, colors of pale cream (0 ppm biguanide) to increasingly intense shades of blue were obtained.

EXAMPLE 4

Example 1 was repeated except that a 0.04% 3', 3", 5',5"-tetrabromo-m-cresolsulfonephthalein and 0.2M citric acid buffer, pH 3.7, was used as the impregnating solution. When test devices were contacted with varying concentration solutions of biguanide as in Example 1, colors of pale yellow green (0 ppm biguanide) to increasingly intense shades of green were obtained.

EXAMPLE 5

Example 1 was repeated except that a 0.1% solution of 3', 3", 5', 5"-tetraiodophenolsulfonephthalein (TIPSP) and 0.2M citrate buffer, pH 3.0, was used as the impregnating solution to make test paper for conversion into test devices. The use of such test devices with varying concentrations of biguanide resulted in a cream color (0 ppm biguanide) to increasingly intense shades of blue at higher concentrations of biguanide.

EXAMPLE 6

Example 1 was repeated except that a 0.05% 3,4,5,6-tetrabromophenolsulfonephthalein (no buffer) was used as an impregnating solution to make test papers for conversion into test devices. The use of such test devices with varying concentrations of biguanide resulted in colors of pale cream to increasingly intense shades of purple blue at higher concentrations of biguanide.

EXAMPLE 7–9

The paper impregnation method used in Example 1 was repeated except that the following compositions were used:

| Example | Indicator | Buffer | pH |
|---------|-----------|--------|----|
| 7 | TIPSP | Citrate | 3 |
| 8 | TBPSP | Citrate | 3 |
| 9 | TBPB* | Citrate | 3 |

*Tetrabromophenol blue

In each Example the impregnated paper was attached to double faced pressure sensitive tape, cut into one ⅓ inch squares and the squares attached to one end on a strip of plastic foil which served as a handle for the test devices. FIGS. 5 and 6 show the structure of such test devices. In use, the test devices were immersed into solutions of biguanide as shown below, moved back and forth in such solutions for thirty (30) seconds with the following color development:

| Biguanide Concentration | Color |
|-------------------------|-------|
| 0 ppm | Pale Yellow |
| 15 ppm | Yellow Green |
| 30 ppm | Green Yellow |
| 50 ppm | Pale Blue |
| 70 ppm | Dark Blue |

What is claimed is:

1. A method for the determination of polymeric biguanides in aqueous test fluids comprising:

A. contacting an aqueous test fluid with a matrix incorporated with a test reagent composition comprising a pH sensitive indicator material which changes from one color to another over a normal range of pH values which normal range is shifted to a measurably different range in the presence of and proportional to the amount of polymeric biguanide present in the aqueous test fluid, and a buffer for maintaining the aqueous test fluid contacting the test reagent composition in the matrix at a constant defined pH value substantially within the normal range of pH values for the indicator material;

B. measuring the color exhibited by the indicator material in the matrix as a result of the presence and amount of polymeric biguanide in the aqueous test fluid; and, C. converting the color exhibited to concentration of polymeric biguanide present in the aqueous test fluid.

2. A method as in claim 1 in which the buffer for maintaining the pH of the test composition upon contact with the aqueous test fluid is set near the edge limit of the said normal pH range.

3. A method as in claim 1 wherein the buffer is included with the indicator material as a component of the test reagent composition in the matrix.

4. A method as in claim 1 wherein the buffer is added to the aqueous test fluid prior to contacting the test reagent composition in the matrix therewith.

5. A method as in claim 1 wherein the indicator material is selected from the group consisting of bromothymol blue, bromophenol blue, bromocresol green, bromochlorophenol blue, bromocresol purple, 3,4,5,6-tetrabromophenolphthalein, ethyl ester, tetrabromophenol blue, and 3', 3", 5', 5"-tetraiodophenolsulfonephthalein. tetrabromophenolphthalein.

6. A method as in claim 1 wherein the matrix is absorbent paper.

7. A method for the determination of low concentrations of polymeric biguanides in aqueous test fluids comprising:

A. causing a predetermined quantity of an aqueous test fluid to flow through a porous matrix having a substantially flat surface area, the matrix containing the dried residue of a test reagent composition comprising a pH sensitive color indicator material which changes from one color to another over a normal range of pH values which normal range is shifted to a measurably different range in the presence of and proportional to the amount of biguanide present in the fluid being tested, and a buffer for maintaining the aqueous test fluid contacting the test reagent composition in the porous matrix at a constant defined pH value substantially within the said normal range of pH values for said indicator material;

B. measuring the color exhibited on the flat surface of the porous matrix as a result of the presence and amount of polymeric biguanide in the aqueous test fluid; and, C. converting the color exhibited on the flat surface of the porous matrix to concentration of polymeric biguanide in the aqueous test fluid.

8. A method as in claim 7 wherein the buffer for maintaining the pH of the test composition upon contact with the aqueous test fluid is set near the edge limit of the said normal pH range.

9. A method as in claim 7 wherein the buffer is included with the indicator material as a component of the test reagent composition in the porous matrix.

10. A method as in claim 7 wherein the buffer is added to the aqueous test fluid prior to contacting the test reagent composition in the porous matrix with the aqueous test fluid.

11. A method as in claim 7 wherein said flow is the result of movement of the matrix through the test fluid.

12. A method as in claim 7 wherein the porous matrix is an absorbent material and the predetermined amount of test fluid flow therethrough is proportional to the volume of fluid being absorbed by the matrix.

13. A method as in claim 12 wherein the absorbent material is paper.

\* \* \* \* \*